United States Patent [19]

Eino

[11] Patent Number: 4,819,065
[45] Date of Patent: Apr. 4, 1989

[54] ELECTRONIC ENDOSCOPE APPARATUS

[75] Inventor: Teruo Eino, Hachioji, Japan

[73] Assignee: Olympus Optical Co., Ltd., Tokyo, Japan

[21] Appl. No.: 41,861

[22] Filed: Apr. 23, 1987

[30] Foreign Application Priority Data

May 8, 1986 [JP] Japan .................................. 61-105297

[51] Int. Cl.⁴ ................................................ A61B 1/04
[52] U.S. Cl. ............................................ 358/98; 128/6
[58] Field of Search ............................. 358/98; 128/6

[56] References Cited

PUBLICATIONS

Fairchild Semiconductor "TV Sync Generator 3261" Data Sheet, 1972.
*IEEE Transactions on Biomedical Engineering,* vol. BME-25, No. 2, Mar. 1978, pp. 208–210, "An Abdominal CCD Camera for the Continuous Video Recording of Sheep Ovary Images During the Reproductive Cycle", H. J. Benoit et al.

*Primary Examiner*—Howard W. Britton
*Attorney, Agent, or Firm*—Ladas & Parry

[57] ABSTRACT

An electronic endoscope apparatus including an endoscope having a distal end portion in which a solid state image sensor is arranged, a signal-processing circuit for processing an image signal output from the solid state image sensor, and a monitor for displaying, as an endoscopic image, a video signal supplied from the signal-processing circuit. The number of vertical pixels of the solid state image sensor is less than the number of scanning lines displayed on the screen of the monitor, whereby all of the image signals supplied from the solid state image sensor are utilized for the image displayed on the monitor.

11 Claims, 3 Drawing Sheets

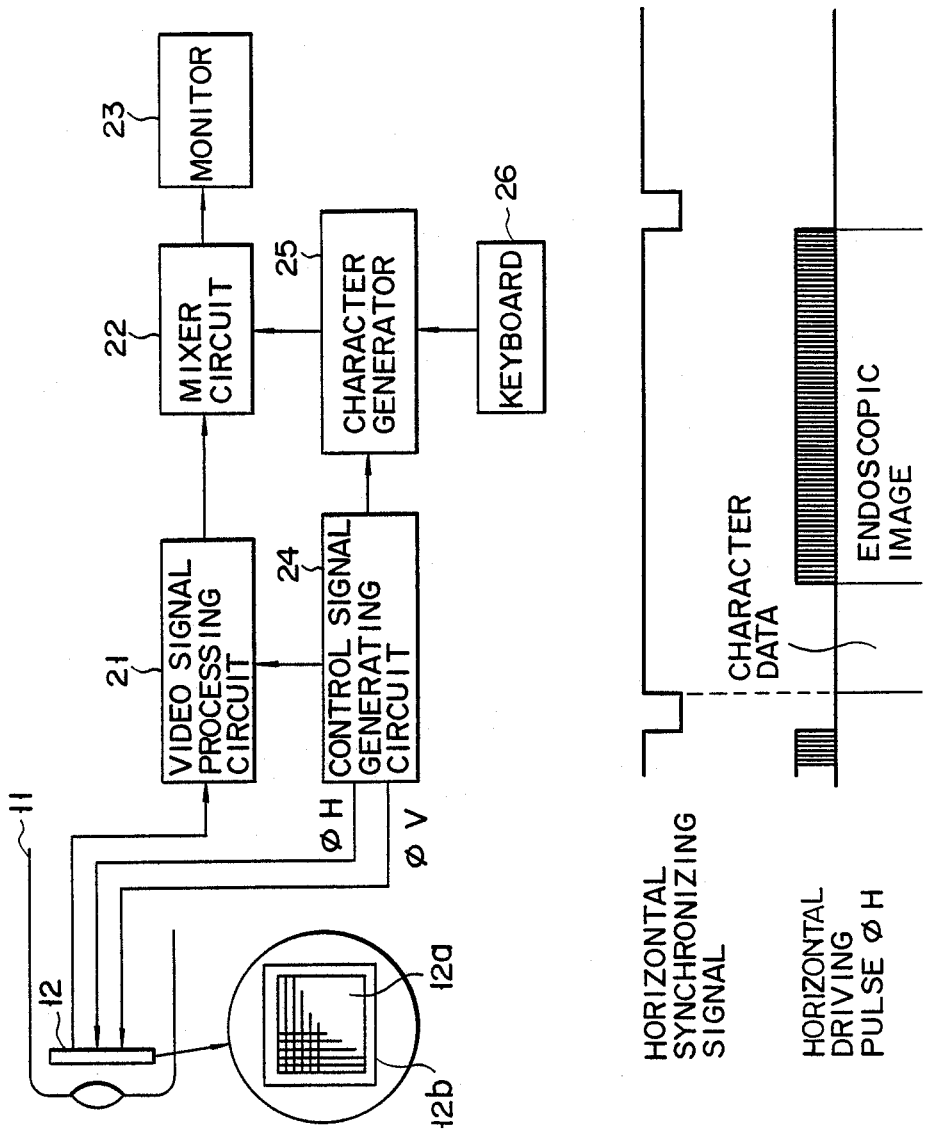

ELECTRONIC ENDOSCOPE APPARATUS

BACKGROUND OF THE INVENTION

The present invention relates to an endoscope apparatus and, more particularly, to an electronic endoscope apparatus having a solid state image sensor arranged in the distal end thereof.

An electronic endoscope apparatus has a solid state image sensor arranged in the distal end portion thereof, so that image signals obtained from the image sensor are displayed on a monitor as an endoscopic image. The endoscopic image is displayed on the right, left, or central portion of the screen of the monitor, and character data concerning a patient under examination, etc. is displayed on the other blank part of the screen.

Preferably, the solid state image sensor of the electronic endoscope apparatus may be constructed such that number nV of its vertical pixels is equal to that of the scanning lines of the standard type TV set (e.g., the NTSC type), and that the horizontal resolution and the vertical resolution are almost equal to each other. However, since the monitor screen is not a perfect rectangle, an image of a smaller area than the area of the image actually picked-up by the image sensor is displayed on the screen. However, since the outline of the endoscopic image and the monitor screen are of different proportions, the endoscopic image cannot be displayed in its entirety on the monitor screen. Thus, there is always some part of the imaging area of the image sensor which is not displayed. In order to eliminate this problem, the solid state image sensor may be designed according to the length-to-width (nV-to-nH) ratio 3 : 4 of the monitor screen such that the endoscopic image covers only the area of the length-to-width ratio nV : nH''(=$\frac{3}{4}$×nH).

However, current semiconductor technology has its limits as regards the miniaturization of pixels of a solid state image sensor. The conventional solid state image sensor described above is not small enough to be able to be fitted in the distal end of the endoscope. As a result, the diameter of the distal end of the endoscope cannot be reduced.

SUMMARY OF THE INVENTION

The object of the present invention is to provide an electronic endoscope apparatus which can reduce in diameter its distal end portion.

According to the invention, an electronic endoscope apparatus is provided with a solid state image sensor, arranged in the distal end portion of an endoscope, whose vertical pixels are less than the number of scanning lines displayed on a screen of a monitor. A video signal-processing circuit causes all the image signals obtained from the solid state image sensor to be displayed on the monitor screen.

The number of pixels of the solid state image sensor arranged in the distal end portion of the endoscope is set so as to substantially equal the number of pixels of an endoscopic image actually displayed on the monitor screen, for example, 380×380 pixels. It is therefore possible to use a smaller-sized solid state image sensor, thereby enabling the diameter of the distal end portion of the endoscope to be decreased.

BRIEF DESCRIPTION OF THE DRAWINGS

FIG. 1 is a block diagram showing an electronic endoscope apparatus according to one embodiment of the present invention;

FIG. 2 is a view showing a horizontal synchronizing signal and a horizontal driving pulse;

DETAILED DESCRIPTION OF THE PREFERRED EMBODIMENTS

Figure 3:
FIG. 3 is a view showing a vertical driving pulse.

In FIG. 1, solid state image sensor 12, arranged in distal end portion 11 of an endoscope, comprises semiconductor chip 12b having imaging area 12a. The number of vertical pixels in imaging area 12a is to the number of the scanning lines displayed on image display area 14 located inwardly of monitor screen 13, as indicated by the broken line in FIG. 5, for example, 380×380 pixels in case of using a NTSC type monitor. The image signal-output terminal of image sensor 12 is connected to monitor 23 via video signal-processing circuit 21 and mixer circuit 22. Image sensor 12 has vertical and horizontal driving terminals connected to control signal-generating circuit 24, which applies horizontal driving pulse φH and vertical driving pulse φV to image sensor 12, and also applies a control signal to video signal-processing circuit 21 and character generator 25. Character generator 25 generates a character signal in response to character data input through keyboard 26.

In the apparatus of FIG. 1, control signal-generating circuit 24 outputs horizontal driving pulse φH and vertical driving pulse φV to solid state image sensor 13, as described above. The pulse width of the horizontal driving pulse φH is less than the horizontal period of a horizontal synchronizing signal. This limited period corresponds to area 14 in which an endoscopic image is displayed (FIG. 5). as is shown in FIG. 3, vertical driving pulse φV includes a high-level period which corresponds to a vertical period of screen 13, except for those periods corresponding to upper and lower blank portions located vertically outside of image display area 14.

Figure 5:
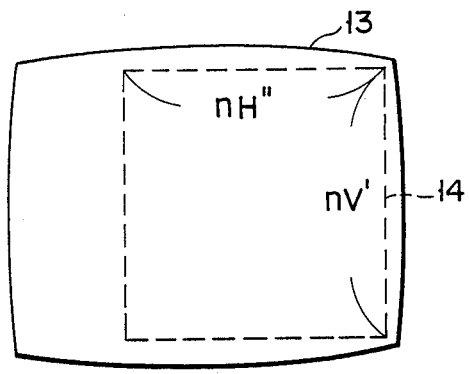
FIGS. 5, 6, and 7 are views showing various relationships between a screen of a monitor and an imaging area of a solid state image sensor.

When image sensor 12 is driven by horizontal and vertical driving pulses φH and φV, it outputs an image signal at the image signal-output terminal. This image signal is supplied to video signal-processing circuit 21 and is processed thereby. The image signal from processing circuit 21, i.e., the video signal, is applied via mixer circuit 22 to monitor 23 and is displayed as an endoscopic image in area 14, as is shown in FIG. 5. In this manner, the entire image picked up on the surface of imaging area 12a of image sensor 12 is displayed in area 14 of the monitor screen.

In response to character data input through keyboard 26, character generator 25 outputs a character signal to mixer circuit 22. Mixer circuit 22 mixes the character signal with the video signal, and supplies the mixed signal to monitor 23. Monitor 23 displays character data relating to a patient under examination, etc., in a screen area leftward of the endoscopic image displayed in area 14 (FIG. 5).

As is described above, solid state image sensor 12 has imaging area 12a (having 380×380 pixels, for example) which corresponds only to that image display area 14 of monitor 23 on which the endoscopic image is actually displayed. Therefore, the apparatus can use a smaller-sized solid state image sensor, and an endoscopic image can be displayed with satisfactory resolution on monitor 23.

Figure 4:
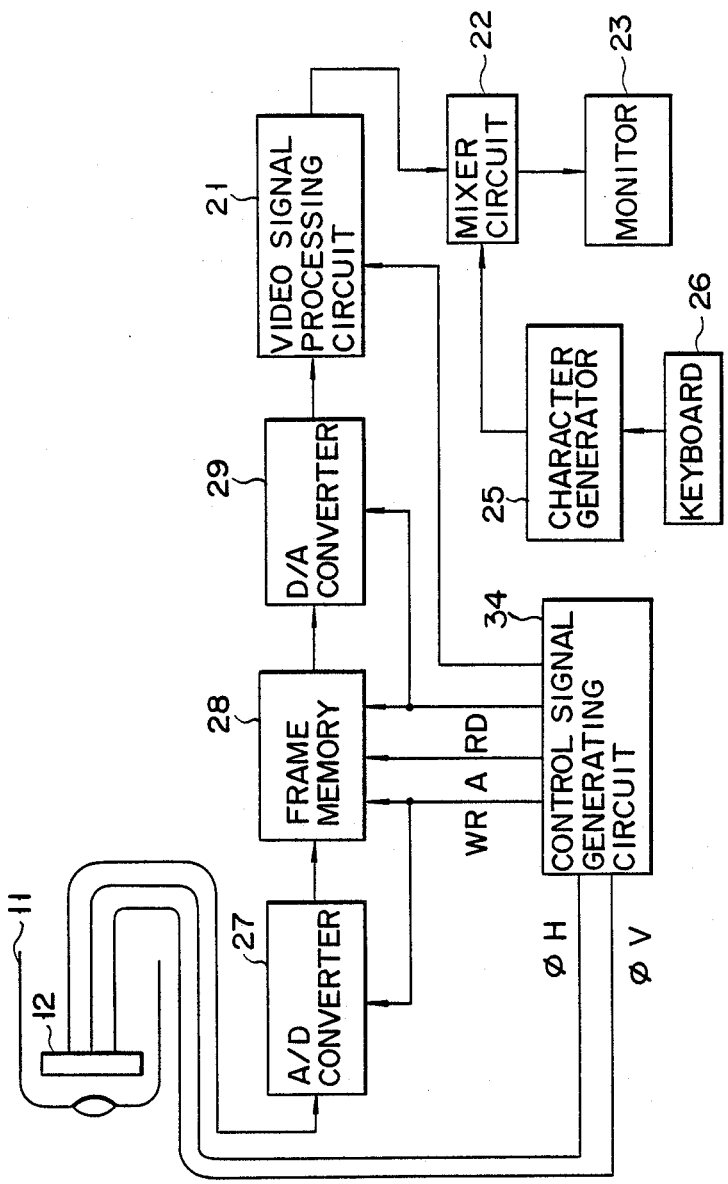
FIG. 4 is a block diagram showing an electronic endoscope apparatus according to another embodiment of the present invention.

According to the embodiment shown in FIG. 4, the image signal-output terminal of image sensor 12 is connected via A/D converter 29 to frame memory 28. Frame memory 28 has a read output terminal which is connected to video signal processing circuit 21 via D/A converter 29.

In this embodiment, horizontal and vertical driving pulses $\phi H$ and $\phi V$ may be generated with a timing other than that shown in FIGS. 2 and 3. Image sensor 12 is driven by horizontal and vertical driving pulses $\phi H$ and $\phi V$, to generate an image signal. A/D converter 27 converts the image signal into a corresponding digital image signal, which is stored in frame memory 28 in response to write signal WR supplied from control signal-generating circuit 34. The image signal stored in frame memory 28 is read out in response to read signal RD and address signal A which are generated with a timing similar to that of the driving pulses shown in FIGS. 2 and 3. These signals are input to frame memory 28 in such a manner that an image picked up by solid state image sensor 12 is displayed on image display area 14 shown in FIG. 5. More specifically, when an image picked up by image sensor 12 is stored in frame memory 28, the reading of the stored image is started at the time when the horizontal line reaches the position corresponding to the upper left end of image display area 14 and is ended at the time when the horizontal line reaches the position corresponding to the upper right end of the same, thereby reading image signals corresponding to one image line. In this manner, the image signals corresponding to all the image lines are read out with the above timing, the resulting endoscopic image is displayed on image display area 14, as is shown in FIG. 5.

Figure 6:
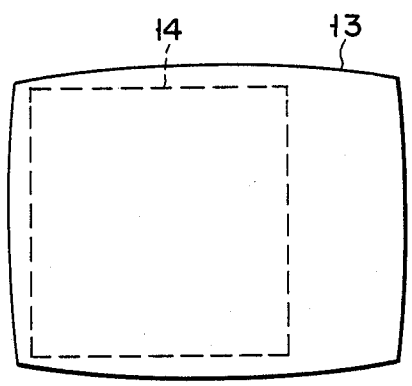
Figure 7:
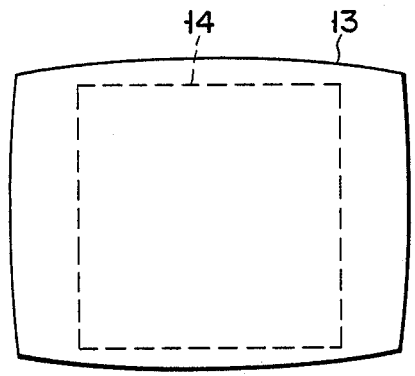

The output timing of read signal RD and address signal A can be set as desired, so that image display area 14 may be located in the left or central part of the monitor screen, as is shown in FIGS. 6 and 7. In FIG. 6, the image read-out is started at the time corresponding approximately to the starting point of the horizontal scanning line. Data thus read out is supplied to monitor 23, via D/A converter 29, video signal-processing circuit 21, and mixer circuit 22. In FIG. 7, the reading out of an image from frame memory 28 is started with a time lag corresponding to the distance between the starting point of the horizontal scanning line and the left end of image display area 14. By thus changing the timing of reading out an image, the image display area can be located in a desired position on screen 13.

As has been described above, in the present invention, the number of pixels of the solid state image sensor is less than the number of horizontal scanning lines displayed on the monitor and substantially equivalent to the screen area in which an endoscopic image is actually displayed. It is therefore possible to use a smaller-sized solid state image sensor and accordingly reduce the diameter of the distal end portion of the endoscope.

What is claimed is:

1. An electronic endoscope apparatus comprising:

an endoscope having a distal end portion in which a solid state image sensor including horizontal and vertical pixels is arranged for generating an image signal;

signal circuit means for driving the solid state image sensor, to cause the same to generate the image signal, processing the image signal output from the solid state image sensor, and for generating a video signal; and display means including a screen for displaying an endoscopic image corresponding to the video signal output from the signal circuit means, by means of a plurality of horizontal scanning lines, wherein the number of vertical pixels of said solid state image sensor is less than the number of scanning lines displayed on the screen of the display means, and said signal circuit means drives the solid state image sensor and processes the image signal in such a manner that all of the image signals obtained from the solid state image sensor are displayed on the screen of the display means.

2. An apparatus according to claim 1, wherein said signal circuit means includes means for supplying the solid state image sensor with a horizontal driving signal having a horizontal period corresponding to the endoscopic image displayed on the screen of the display means.

3. An apparatus according to claim 1, wherein said signal circuit means includes means for supplying the solid state image sensor with a vertical driving signal having a vertical period corresponding to the endoscopic image displayed on the screen of the display means.

4. An apparatus according to claim 1, wherein said signal circuit means includes character generator means for outputting a character signal which is mixed with the video signal corresponding to the endoscopic image displayed on the display means.

5. An apparatus according to claim 4, wherein said display means displays the character signal in an area of the screen other than an image display area for the endoscopic image.

6. An apparatus according to claim 1, wherein said signal circuit means includes drive means for supplying a drive signal to the solid state image sensor, and signal processing means for processing the image signal output from the solid state image sensor.

7. An apparatus according to claim 6, wherein said drive means is means for generating a horizontal driving pulse and a vertical driving pulse which each include a driving period corresponding to each of width and height of an image display area in which the endoscopic image is displayed.

8. An apparatus according to claim 1, wherein said signal circuit means includes memory means which stores the image signal output from the solid state image sensor and corresponding to the endoscopic image displayed on the screen of the display means, and read-out means for reading out the image signal from the memory means.

9. An apparatus according to claim 8, wherein said read-out means is means for outputting an address signal indicative of a predetermined display position on the screen of the display means to said memory means.

10. An apparatus according to claim 9, wherein said read-out means is means for outputting the address signal to the memory means, for reading out the image signal in such a manner that the endoscopic image is displayed on the screen at a location biased to one side thereof.

11. An apparatus according to claim 9, wherein said read-out means is means for outputting the address signal to the memory means, for reading out the image signal in such a manner that the endoscopic image is displayed in a central portion of the screen.

* * * * *